(12) United States Patent
Compas et al.

(10) Patent No.: US 9,943,277 B2
(45) Date of Patent: Apr. 17, 2018

(54) DETECTING CORONARY STENOSIS THROUGH SPATIO-TEMPORAL TRACKING

(71) Applicant: International Business Machines Corporation, Armonk, NY (US)

(72) Inventors: Colin B. Compas, San Jose, CA (US); Tanveer F. Syeda-Mahmood, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 949 days.

(21) Appl. No.: 14/243,106

(22) Filed: Apr. 2, 2014

(65) Prior Publication Data
US 2015/0282777 A1    Oct. 8, 2015

(51) Int. Cl.
G06K 9/46   (2006.01)
A61B 5/00   (2006.01)
A61B 6/00   (2006.01)
G06T 7/00   (2017.01)
G06T 7/174  (2017.01)

(52) U.S. Cl.
CPC .............. *A61B 6/481* (2013.01); *A61B 6/504* (2013.01); *G06T 7/0016* (2013.01); *G06T 7/174* (2017.01); *A61B 6/5217* (2013.01); *G06T 2207/10016* (2013.01); *G06T 2207/10116* (2013.01); *G06T 2207/30101* (2013.01)

(58) Field of Classification Search
None
See application file for complete search history.

(56) References Cited

U.S. PATENT DOCUMENTS 8,411,914 B1 *  4/2013  Mangoubi ............. G06T 7/0012
                                                382/107
8,422,738 B1 *  4/2013  Stastny ................ G06K 9/0063
                                                382/103

(Continued)

FOREIGN PATENT DOCUMENTS

WO         9749065 A1      12/1997

OTHER PUBLICATIONS

T. Giesler et al, "Noninvasive Visualization of Coronary Arteries Using Contrast-Enhanced Multidetector CT: Influence of Heart Rate on Image Quality and Stenosis Detection" American Journal of Roentgenology, vol. 179 (4), pp. 911-916, 2002.

*Primary Examiner* — Patricia Park
(74) *Attorney, Agent, or Firm* — Cantor Colburn LLP (57) ABSTRACT

Embodiments relate to detecting coronary stenosis through spatio-temporal tracking. Aspects include extracting a coronary artery tree from each of a sequence of angiogram images, creating a mean artery tree from the extracted coronary artery trees, and projecting the mean artery tree back onto each of the sequence of angiogram images to recover a complete coronary artery tree for each of the sequence of angiogram images. Aspects also include extracting one or more tubular sections from each of the sequence of angiogram images, estimating an arterial width for each of the one or more tubular sections from each of the sequence of angiogram images, and creating a spatio-temporal surface from the arterial widths of the one or more tubular sections over a time spanned by the sequence of angiogram images. Aspects further include detecting a minimum in the spatio-temporal surface and determining if the minimum is indicative of stenosis.

11 Claims, 12 Drawing Sheets

(56) References Cited

U.S. PATENT DOCUMENTS

| | | | |
|---|---|---|---|
| 2009/0238412 A1* | 9/2009 | Grass | A61B 6/032 382/107 |
| 2010/0128940 A1 | 5/2010 | Buelow et al. | |
| 2011/0103665 A1* | 5/2011 | Gulsun | G06T 7/248 382/131 |
| 2011/0213243 A1 | 9/2011 | Mallya et al. | |
| 2011/0224542 A1 | 9/2011 | Mittal et al. | |
| 2012/0072190 A1* | 3/2012 | Sharma | A61B 5/026 703/2 |
| 2012/0134553 A1 | 5/2012 | Liao et al. | |
| 2013/0253895 A1 | 9/2013 | Okell et al. | |
| 2014/0371578 A1* | 12/2014 | Auvray | A61B 6/12 600/424 |

* cited by examiner

DETECTING CORONARY STENOSIS THROUGH SPATIO-TEMPORAL TRACKING

BACKGROUND

Embodiments of the invention relate generally to automated angiogram analysis, and more specifically, to detecting coronary stenosis through spatio-temporal tracking.

Cardiovascular disease (CVD) results in more death and disability in both males and females in all western societies than any other disease category, accounting for one third of all deaths in the United States in 2007. Any occlusion of these arteries can impact heart function leading to effort intolerance with exertion provoked chest symptoms, heart attack, permanent impairment of heart muscle function, and sudden death.

The "gold standard" diagnostic test for CAD is the coronary angiogram. A coronary angiogram involves placing plastic catheters into the arterial system and injecting iodinated contrast solution into the coronary blood flow, to obtain a silhouette of the coronary arterial wall. The angiographic images are typically recorded at 15 or 30 frames a second, providing a motion picture of the flowing blood and contrast mixture to permit the identification of segmental coronary narrowing or blockage attributable to coronary stenosis, which is a condition in which a coronary artery becomes tapered and backed up with materials like fat or cholesterol.

In general detection of vessels and coronary stenosis in X-ray angiography data is difficult due to the low contrast between vessels and surrounding tissue, as well as large intensity gradients within the image. Interpretation of coronary angiograms is nearly always performed by visual estimation of the severity of narrowing in the diseased coronary artery. In addition, the curvilinear cylindrical structure of an artery and the irregular and often eccentric remaining lumen through the diseased segment make accurate visual detection of stenosis difficult. Often, spurious dye and imaging artifacts can give a false appearance of stenosis in these sequences. To resolve such cases, clinicians watch the angiograms in loops exploiting the fact that a real stenosis will persist in each image frame through time.

BRIEF SUMMARY

Embodiments include a method, system, and computer program product for detecting coronary stenosis through spatio-temporal tracking. The method includes extracting a coronary artery tree from each of a sequence of angiogram images, creating a mean artery tree from the extracted coronary artery trees, and projecting the mean artery tree back onto each of the sequence of angiogram images to recover a complete coronary artery tree for each of the sequence of angiogram images. The method also includes extracting one or more tubular sections from each of the sequence of angiogram images, estimating an arterial width for each of the one or more tubular sections from each of the sequence of angiogram images, and creating a spatio-temporal surface from the arterial widths of the one or more tubular sections over a time spanned by the sequence of angiogram images. The method further includes detecting a minimum in the spatio-temporal surface and determining if the minimum is indicative of stenosis.

Additional features and advantages are realized through the techniques of the present disclosure. Other embodiments and aspects of the disclosure are described in detail herein.

For a better understanding of the disclosure with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The foregoing and other features, and advantages of the disclosure are apparent from the following detailed description taken in conjunction with the accompanying drawings in which:

DETAILED DESCRIPTION

Embodiments described herein are directed to methods, systems and computer program products for automatic detection of coronary stenosis in X-ray angiography data. In exemplary embodiments, the spatio-temporal nature of angiography sequences is used to isolate the coronary artery tree. An arterial width surface is formed for each isolated artery segment by calculating the width along a segment and tracking the segment in each image frame over time. A persistent minima of this surface, which corresponds to a stenosis in the artery, is then identified.

Figure 1:
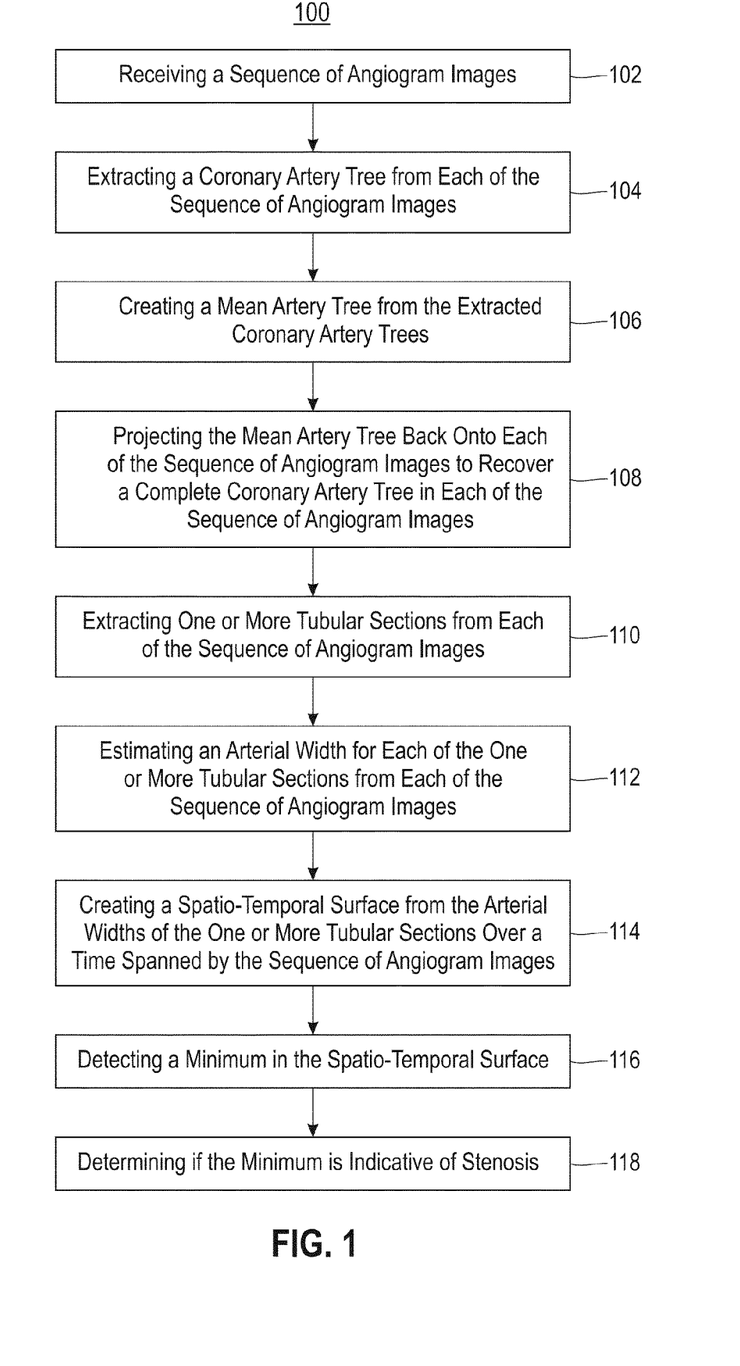
FIG. 1 depicts a process flow for detecting coronary stenosis through spatio-temporal tracking in accordance with an embodiment.

Referring now to FIG. 1, a process flow of a method 100 for detecting coronary stenosis through spatio-temporal tracking in accordance with an embodiment is illustrated. As illustrated at block 102, the method 100 includes receiving a sequence of angiogram images. In exemplary embodiments, the sequence of angiogram images are X-ray angiogram images. Next, as shown at block 104, the method 100 includes extracting a coronary artery tree from each of the sequence of angiogram images. In exemplary embodiments, the extraction of the coronary artery tree from each of the sequence of angiogram images is performed by filtering each angiogram image using RLF filtering. In exemplary embodiments, RLF filtering provides a complete highlighting of coronary arteries including minor segments while still suppressing noise in the angiogram images. In addition, RLF filtering allows robust segmentation and delineation of coronary arteries and bridges any gaps in cases of complete stenosis where the arteries are occluded causing gaps in segmented images. In exemplary embodiments, once the RLF filtering is complete, an adaptive local threshold may be applied to produce an artery tree. In other embodiments, any other suitable known method may be used to extract the coronary artery tree from each of the sequence of angiogram images.

As shown at block 106, the method 100 also includes creating a mean artery tree from the extracted coronary artery trees. In exemplary embodiments, the creation of the mean artery tree from the extracted coronary artery trees is performed by aligning the extracted artery trees from each angiogram image in the sequence of angiogram images. One approach to integrating spatio-temporal information is to track inter-frame motion using methods such as optical flow in which the flow field is computed between consecutive frames. However, in order to find the region containing the coronary artery tree, as many pixel points on the tree as possible should to be found, to 'fill-in' the tree. Accordingly, rather than tracking movement of the coronary artery tree frame-by-frame, a displacement field is calculated for each image in the sequence of angiogram images with respect to a chosen reference image of the sequence. In exemplary embodiments, the reference image may be chosen by an operator or automatically. In exemplary embodiments, to capture motion between frames a multi-scale approach is applied in order to first match a smoothed version of the image to ensure consistency in the image gradients between frames. In exemplary embodiments, optical-flow tracking can be used to align the sequence of images.

Continuing with reference to FIG. 1, as shown at block 108, the method 100 includes projecting the mean artery tree back onto each of the sequence of angiogram images to recover a complete coronary artery tree in each of the sequence of angiogram images. In exemplary embodiments, the displacement fields calculated to align the angiogram images are also used to re-align the identified vessel segments extracted from the mean image back to the original sequence of angiogram images.

Figure 2A:
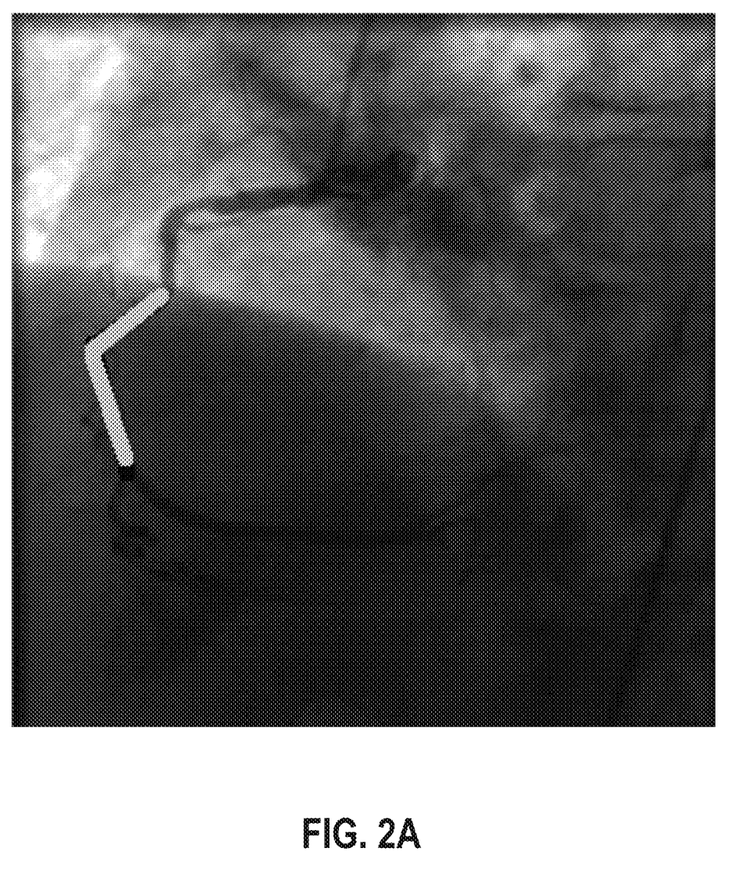
FIG. 2A depicts an angiogram image of a coronary vessel with stenosis in accordance with an embodiment.
Figure 2B:
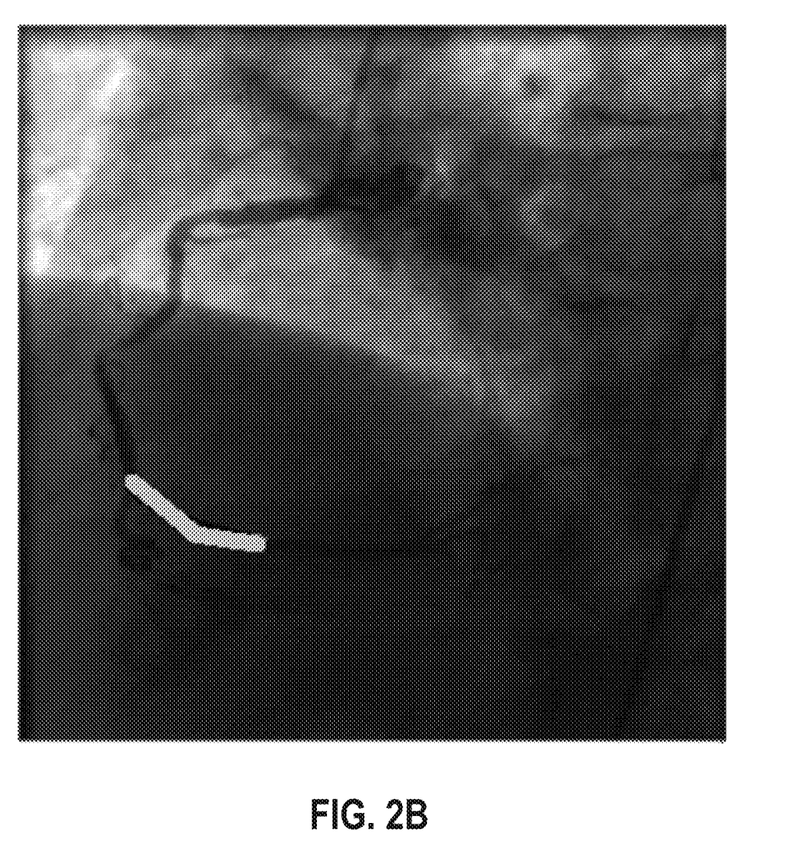
FIG. 2B depicts an angiogram image of a coronary vessel without stenosis in accordance with an embodiment.
Figure 2C:
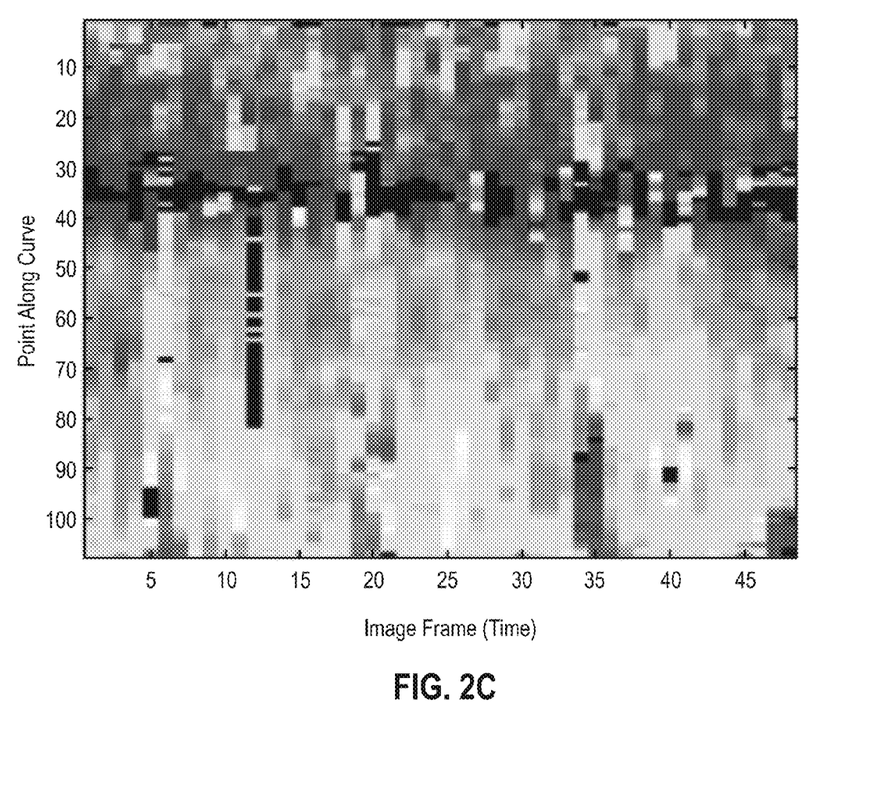
FIG. 2C depicts a visual representation of the width measurements along of the coronary vessel of FIG. 2A across a period of time in accordance with an embodiment.
Figure 2D:
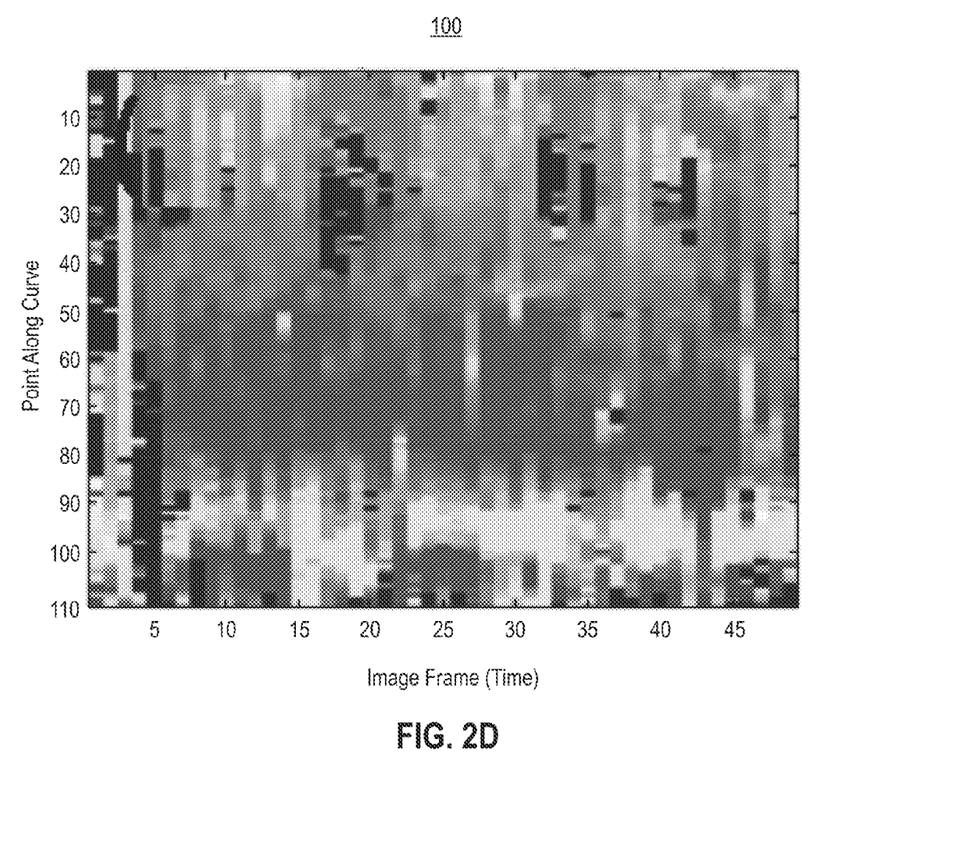
FIG. 2D depicts a visual representation of the width measurements along of the coronary vessel of FIG. 2B across a period of time in accordance with an embodiment.

Continuing with reference to FIG. 1, as illustrated at block 110, the method 100 also includes extracting one or more tubular sections from each of the sequence of angiogram images. For example, FIG. 2A depicts an angiogram image having an extracted segment showing a coronary vessel with stenosis and FIG. 2B depicts an angiogram image of a having an extracted segment showing coronary vessel without stenosis. Next, as shown at block 112, the method 100 includes estimating an arterial width for each of the one or more artery segments from each of the sequence of angiogram images. In exemplary embodiments, after re-aligning the mean artery tree back to each of the sequence of angiogram images, the widths along the individual curves are calculated by finding the distance to the boundary image perpendicular to the vessel segment. This results in a set of widths along a common set of artery segments that can be compared over time. In exemplary embodiments, the individual width values for the one or more tubular sections are placed into a matrix in which the dimensions of the matrix are a point along the artery segment and a time corresponding to the timestamp of the image. The values in the matrix are the vessel width corresponding to that point in time and the point along the artery segment. For example, FIG. 2C depicts a visual representation of the width measurements along of the coronary vessel of FIG. 2A across a period of time spanned by the sequence of images and FIG. 2D depicts a visual representation of the width measurements along of the coronary vessel of FIG. 2B across a period of time spanned by the sequence of images.

Figure 2E:
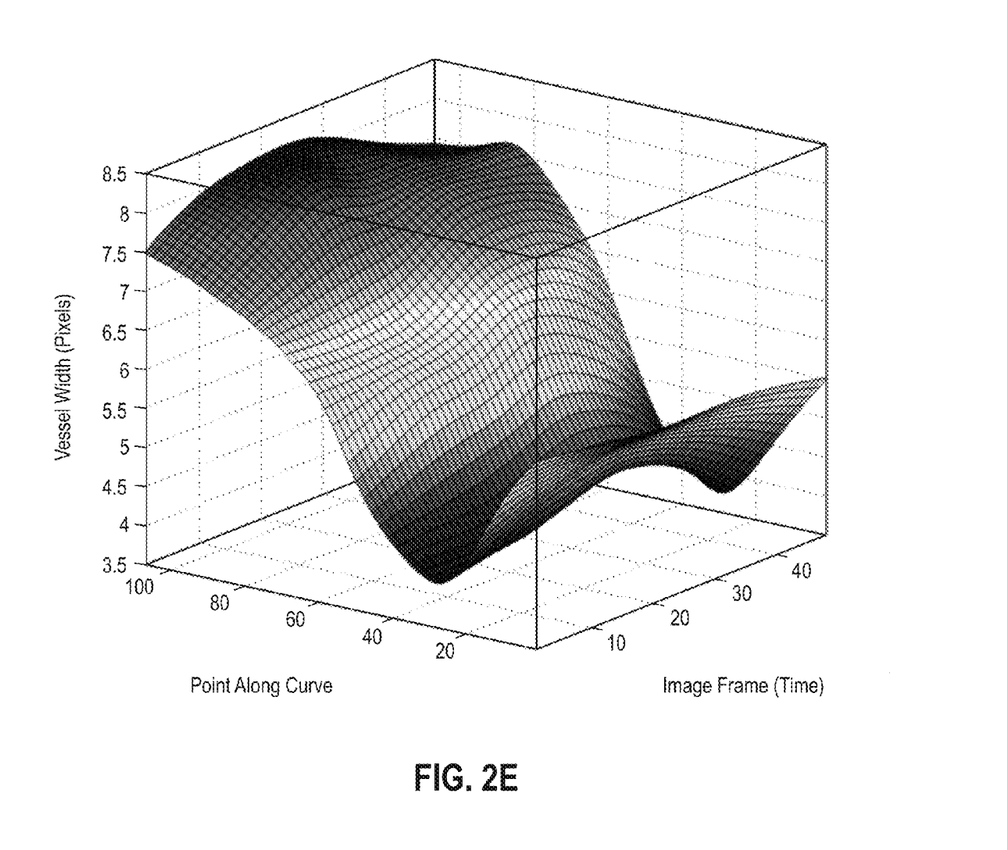
FIG. 2E depicts a three dimensional surface based on the values in FIG. 2C in accordance with an embodiment.
Figure 2F:
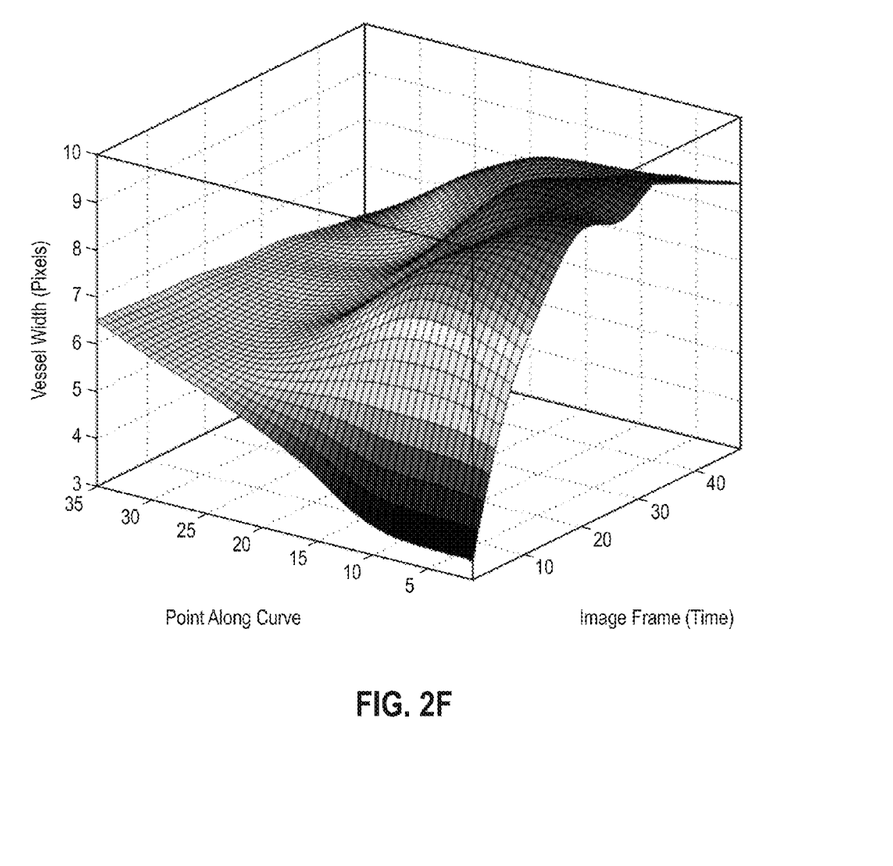
FIG. 2F depicts a three dimensional surface based on the values in FIG. 2D in accordance with an embodiment.

As illustrated at block 114, the method 100 also includes creating a spatio-temporal surface from the arterial widths of the one or more tubular sections over a time spanned by the sequence of angiogram images. For example, FIG. 2E depicts a three dimensional surface based on the values in FIG. 2C and FIG. 2F depicts a three dimensional surface based on the values in FIG. 2D.

In the case of stenosis a minimum vessel width value should occur at the same point in this matrix at each time point. However, due to noise in the vessel width measurements, this minimum may be difficult to detect in the raw width values. For example, artery segments are shown in FIGS. 2A and 2B and width matrices corresponding to the artery segments are shown in FIGS. 2C and 2D, respectively. FIG. 2A, illustrates an artery segment that contains a stenosis, while FIG. 2B illustrates a normal segment. In exemplary embodiments, in order to overcome the noise in the angiogram images and data, a 2D spline surface is constructed based on the raw width values. Exemplary width surfaces for the raw values corresponding to the width matrices of FIGS. 2C and 2D are shown in FIGS. 2E and 2F, respectively. By displaying the width in the Z dimension, a clear valley appears in the surface containing a stenosis. This valley corresponds to the point along the artery segment where the stenosis occurs.

Figure 2G:
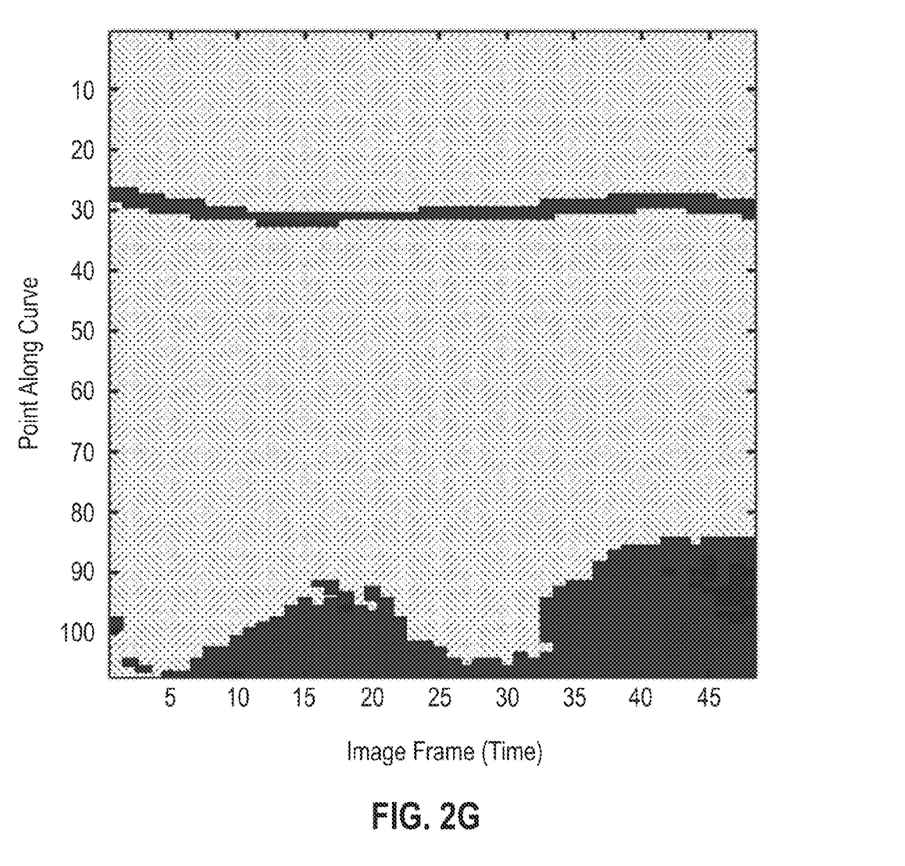
FIG. 2G depicts a map illustrating where the derivative of the three dimensional surface shown in FIG. 2E is approximately zero in accordance with an embodiment.
Figure 2H:
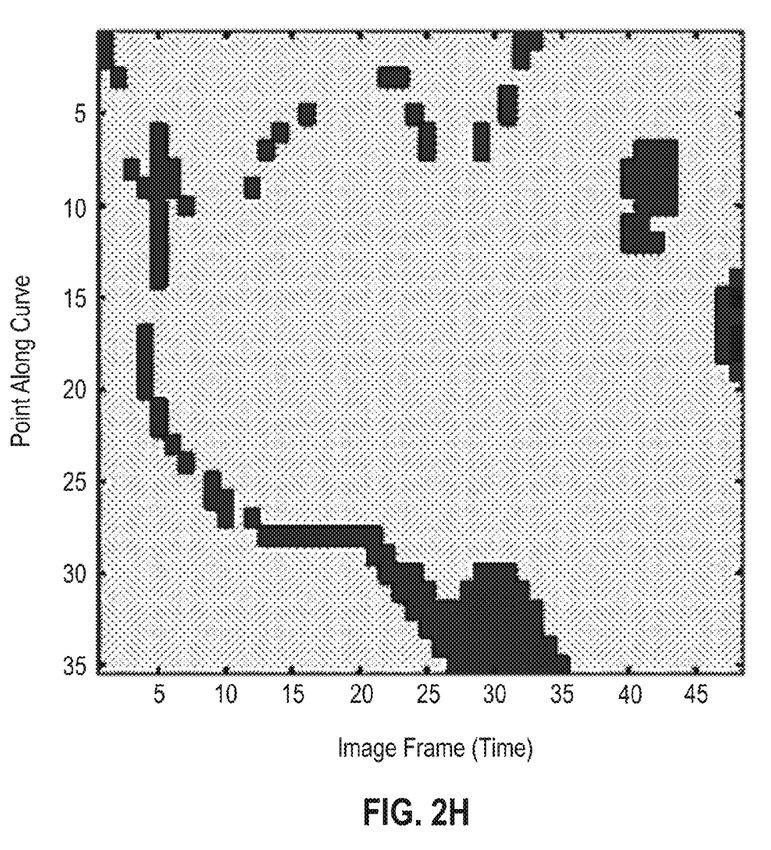
FIG. 2H depicts a map illustrating where the derivative of the three dimensional surface shown in FIG. 2F is approximately zero in accordance with an embodiment.
Figure 2I:
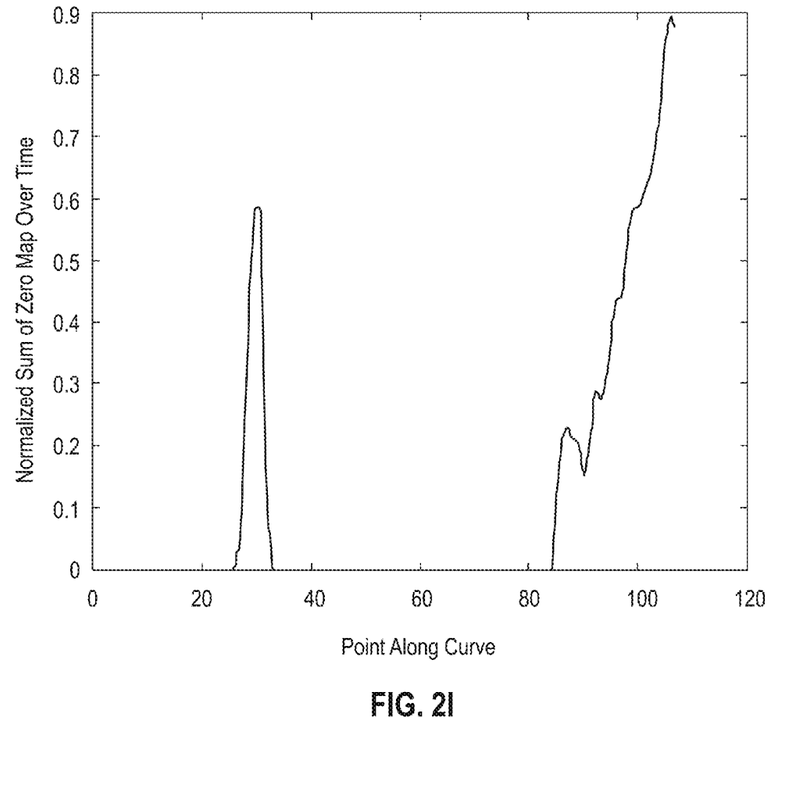
FIG. 2I depicts a graph illustrating normalized sum of the map shown in FIG. 2H over time in accordance with an embodiment.
Figure 2J:
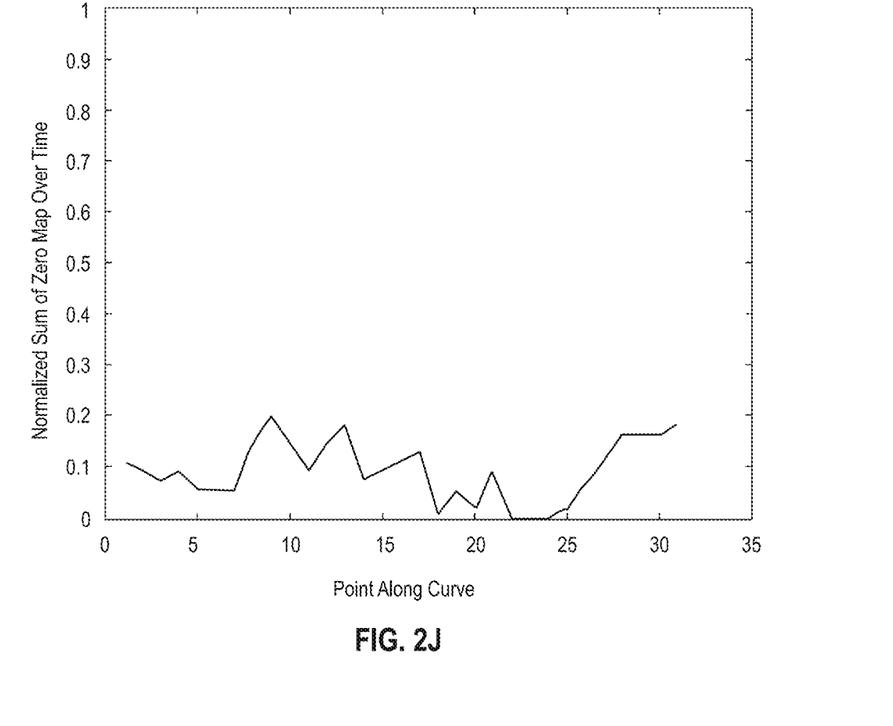
FIG. 2J depicts a graph illustrating normalized sum of the map shown in FIG. 2G over time in accordance with an embodiment.

Continuing with reference to FIG. 1, as shown at block 116, the method 100 includes detecting a minimum in the spatio-temporal surface. In exemplary embodiments, the minimum is detected using 3D spline approximation and horizontal line detection. In exemplary embodiments, in order to detect the minimum of the surface the point at which the derivative of the width surface along the artery direction is equal to, or close to, zero is identified. FIGS. 2G and 2H illustrate graphs of the zero points in the surface derivative the stenosis and normal cases shown in FIGS. 2A and 2B, respectively. In exemplary embodiments, the zero map is projected into a single vector along the curve in order to detect a peak where the stenosis occurs. These projections along the curve are shown in FIGS. 2I and 2J, respectively.

As illustrated at block 118, the method 100 also includes determining if the minimum is indicative of stenosis. In exemplary embodiments, determining if the minimum is indicative of stenosis is performed by inspecting a vertical projection histogram of the derivative of the 3D spline surface. In exemplary embodiments, a curve representing an ideal stenosis, which is a sharply peaked Gaussian, is compared with the zero projections, such as those shown in FIGS. 2I and 2J, and the peak correlation can be used to identify stenosis. In exemplary embodiments, the parameters of the ideal stenosis curve for width and height can be tuned based on experimental data.

In exemplary embodiments, to extract the tubular regions from the skeletal curves, boundary pixels on either side of the skeletal curve are identified that are in the direction normal to each skeletal point along the curve. Each coronary artery segment $C_i$ is represented by an ordered set of skeletal points $\{(x, y, \delta_1, \delta_2, \theta)\}$ where $(x,y) \in S_i$ is a skeletal pixel on the skeletal curve $S_i$ passing through the tubular segment, and $\delta_1$ and $\delta_2$ are the units along the surface normal $\theta$ at which the tubular boundary points are found. The widths of the artery segments are then calculated as the distance between the intersection of surface normal and the point of the artery centerline as $W_i=(\delta_{2i}-\delta_{1i})$.

In one example, a coronary artery segment is extracted that contains a stenosis at time t. If the segment is well-isolated, and denoting the parametric representation of the curve through a parameter s, points (x(s),y(s),t) are sampled along the centerline and the arterial width W (s) is computed at each such point. The corresponding points for the artery segment in the next image of the sequence at time t' are (x'(s),y'(s),t'). Accordingly, the width values along the curve for each image frame in time can be determined and analyzed. In the raw data format, these widths can be very noisy and difficult to interpret. By fitting a surface using local linear regression to the raw values a much clearer picture of the behavior of the vessel widths across time can be created, as seen in FIGS. 2E and 2F. The minima of this surface can then be found by taking the analytic derivative at each point along the curve and looking for places where the derivative is approximately zero to produce the zero-map, shown in FIGS. 2G and 2H. When the coronary artery depicts no stenosis, the map does not show a persistent marked minima, FIG. 2H.

In exemplary embodiments, in order to detect a horizontal pattern the sum of the zero-map along the curve is calculated. If the stenotic regions of the vessel were all perfectly aligned this would result in a box function at the point along the curve where the stenosis occurs. Since there is some drift due to the alignment of the vessel segments the peak in this curve will be more Gaussian in nature. The width of the Gaussian corresponds to how much the location of the stenosis varies over time. If the variance in position of the minima becomes too large then the valley in the surface is not likely to be a stenosis and may be due to an image artifact. As a result the width of the peak in the mean zero curve is a parameter that needs to be set for detecting a stenosis. Additionally, the magnitude of the peak is an indication of how persistent the peak is over time.

By normalizing the sum of the zero-map by the number of image frames, the magnitude will be equal to one indicating that the stenosis persists across the entire image sequence. Since the stenosis should be present across time, a high magnitude is indicative of stenosis in the projection. FIGS. 2I and 2J illustrate the mean projections for the two corresponding zero-maps shown in FIGS. 2G and 2H, respectively. A peak is detected to locate the stenosis by correlating the mean curve with a peaked Gaussian curve that exhibits the identified behavior. By varying the magnitude and width of this function, the algorithm can be made more or less restrictive in identifying a possible stenosis. In one embodiment, the values used for the ideal stenosis may be a height of 70% and $\sigma=1.5$. However, as will be appreciated by those of ordinary skill in the art these parameters can be tuned depending on the severity of stenosis to detect.

Figure 3:
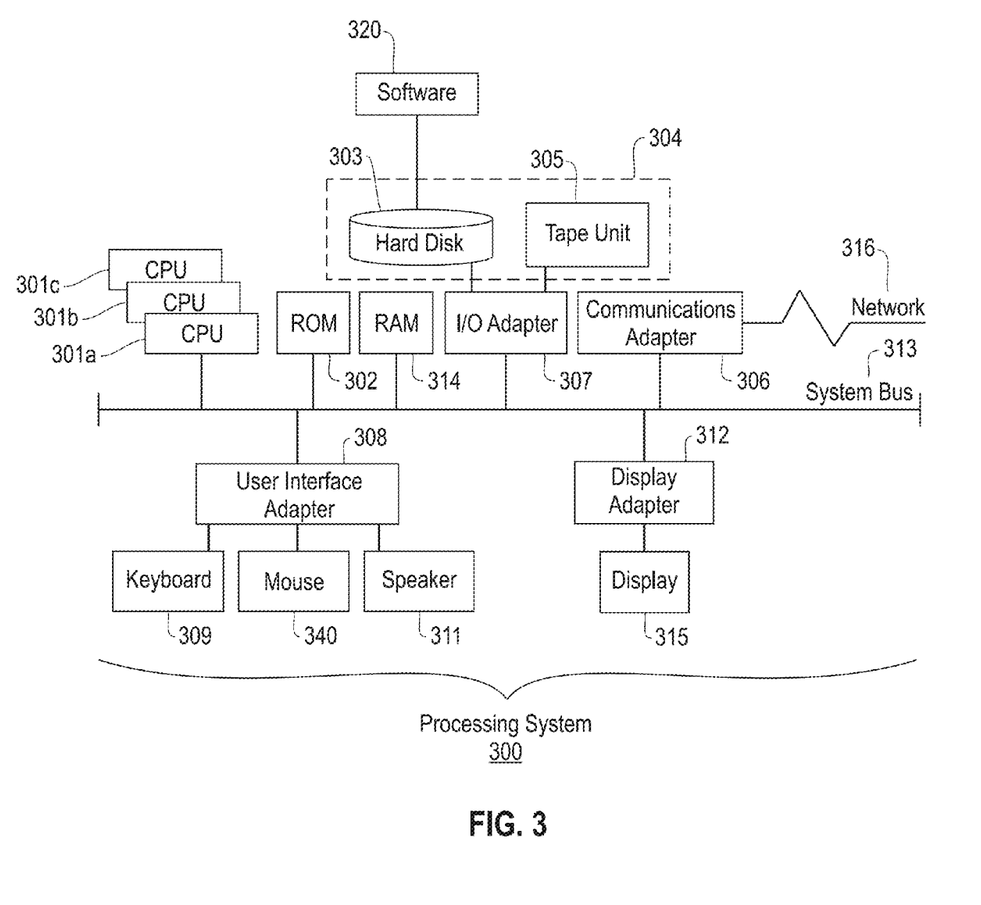
FIG. 3 depicts a processing system for practicing the teachings herein in accordance with an embodiment.

Referring to FIG. 3, there is shown an embodiment of a processing system 300 for implementing the teachings herein. In this embodiment, the system 300 has one or more central processing units (processors) 301a, 301b, 301c, etc. (collectively or generically referred to as processor(s) 301). In one embodiment, each processor 301 may include a reduced instruction set computer (RISC) microprocessor. Processors 301 are coupled to system memory 314 and various other components via a system bus 313. Read only memory (ROM) 302 is coupled to the system bus 313 and may include a basic input/output system (BIOS), which controls certain basic functions of system 300.

FIG. 3 further depicts an input/output (I/O) adapter 307 and a network adapter 306 coupled to the system bus 313. I/O adapter 307 may be a small computer system interface (SCSI) adapter that communicates with a hard disk 303 and/or tape storage drive 305 or any other similar component. I/O adapter 307, hard disk 303, and tape storage device 305 are collectively referred to herein as mass storage 304. Software 320 for execution on the processing system 300 may be stored in mass storage 304. A network adapter 306 interconnects bus 313 with an outside network 316 enabling data processing system 300 to communicate with other such systems. A screen (e.g., a display monitor) 315 is connected to system bus 313 by display adaptor 312, which may include a graphics adapter to improve the performance of graphics intensive applications and a video controller. In one embodiment, adapters 307, 306, and 312 may be connected to one or more I/O busses that are connected to system bus 313 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 313 via user interface adapter 308 and display adapter 312. A keyboard 309, mouse 130, and speaker 311 all interconnected to bus 313 via user interface adapter 308, which may include, for example, a Super I/O chip integrating multiple device adapters into a single integrated circuit.

Thus, as configured in FIG. 3, the system 300 includes processing capability in the form of processors 301, storage capability including system memory 314 and mass storage 304, input means such as keyboard 309 and mouse 130, and output capability including speaker 311 and display 315. In one embodiment, a portion of system memory 314 and mass storage 304 collectively store an operating system such as the AIX® operating system from IBM Corporation to coordinate the functions of the various components shown in FIG. 3.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

Further, as will be appreciated by one skilled in the art, aspects of the present disclosure may be embodied as a system, method, or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method for detecting coronary stenosis through spatio-temporal tracking comprising:
   extracting a coronary artery tree from each of a sequence of angiogram images obtained from a patient;
   creating a mean artery tree from the extracted coronary artery trees by aligning the extracted artery trees from each angiogram image in the sequence of angiogram images and calculating a displacement field for each image in the sequence of angiogram images with respect to a reference image of the sequence of angiogram images;
   projecting the mean artery tree back onto each of the sequence of angiogram images to recover a complete coronary artery tree for each of the sequence of angiogram images;

extracting one or more tubular sections from each of the sequence of angiogram images, wherein extracting the coronary artery tree from each of the sequence of angiogram images comprises filtering each angiogram image using RLF filtering;

estimating an arterial width for each of the one or more tubular sections from each of the sequence of angiogram images;

creating a spatio-temporal surface from the arterial widths of the one or more tubular sections over a time spanned by the sequence of angiogram images;

detecting a minimum in the spatio-temporal surface; and determining if the minimum is indicative of stenosis.

2. The method of claim 1, wherein the arterial widths for each of the one or more tubular sections are calculated by finding a distance to a boundary image perpendicular to the one or more tubular sections.

3. The method of claim 1, wherein determining if the minimum is indicative of stenosis comprises inspecting a vertical projection histogram of a derivative of the spatio-temporal surface.

4. The method of claim 3, wherein a curve representing an ideal stenosis is a sharply peaked Gaussian.

5. A computer program product for detecting coronary stenosis through spatio-temporal tracking, the computer program product comprising a non-transitory computer readable storage medium having program code embodied therewith, the program code executable by a processor to:

extract a coronary artery tree from each of a sequence of angiogram images obtained from a patient, wherein extracting the coronary artery tree from each of the sequence of angiogram images comprises filtering each angiogram image using RLF filtering;

create a mean artery tree from the extracted coronary artery trees by aligning the extracted artery trees from each angiogram image in the sequence of angiogram images and calculating a displacement field for each image in the sequence of angiogram images with respect to a reference image of the sequence of angiogram images;

project the mean artery tree back onto each of the sequence of angiogram images to recover a complete coronary artery tree for each of the sequence of angiogram images;

extract one or more tubular sections from each of the sequence of angiogram images;

estimate an arterial width for each of the one or more tubular sections from each of the sequence of angiogram images;

create a spatio-temporal surface from the arterial widths of the one or more tubular sections over a time spanned by the sequence of angiogram images;

detect a minimum in the spatio-temporal surface; and determine if the minimum is indicative of stenosis.

6. The computer program product of claim 5, wherein the arterial widths for each of the one or more tubular sections are calculated by finding a distance to a boundary image perpendicular to the one or more tubular sections.

7. The computer program product of claim 5, wherein determining if the minimum is indicative of stenosis comprises inspecting a vertical projection histogram of a derivative of the spatio-temporal surface.

8. The computer program product of claim 7, wherein a curve representing an ideal stenosis is a sharply peaked Gaussian.

9. A system for detecting coronary stenosis through spatio-temporal tracking comprising:

a memory having computer readable computer instructions; and a processor for executing the computer readable instructions, the instruction including:

extracting a coronary artery tree from each of a sequence of angiogram images, wherein extracting the coronary artery tree from each of the sequence of angiogram images comprises filtering each angiogram image using RLF filtering;

creating a mean artery tree from the extracted coronary artery trees by aligning the extracted artery trees from each angiogram image in the sequence of angiogram images and calculating a displacement field for each image in the sequence of angiogram images with respect to a reference image of the sequence of angiogram images;

projecting the mean artery tree back onto each of the sequence of angiogram images to recover a complete coronary artery tree for each of the sequence of angiogram images;

extracting one or more tubular sections from each of the sequence of angiogram images;

estimating an arterial width for each of the one or more tubular sections from each of the sequence of angiogram images;

creating a spatio-temporal surface from the arterial widths of the one or more tubular sections over a time spanned by the sequence of angiogram images;

detecting a minimum in the spatio-temporal surface; and determining if the minimum is indicative of stenosis.

10. The system of claim 9, wherein determining if the minimum is indicative of stenosis comprises inspecting a vertical projection histogram of a derivative of the spatio-temporal surface.

11. The system of claim 10, wherein a curve representing an ideal stenosis is a sharply peaked Gaussian.

* * * * *